United States Patent
Mazzolla et al.

(10) Patent No.: US 8,066,729 B2
(45) Date of Patent: Nov. 29, 2011

(54) SURGICAL OBTURATOR

(75) Inventors: Richard V. Mazzolla, Hardwick, NJ (US); Michael T. Patton, Austin, TX (US)

(73) Assignee: Stryker Corporation, San Jose, CA (US)

(*) Notice: Subject to any disclaimer, the term of this patent is extended or adjusted under 35 U.S.C. 154(b) by 1004 days.

(21) Appl. No.: 10/890,078

(22) Filed: Jul. 13, 2004

(65) Prior Publication Data

US 2005/0209623 A1 Sep. 22, 2005

Related U.S. Application Data

(60) Provisional application No. 60/549,199, filed on Mar. 2, 2004.

(51) Int. Cl.
*A61B 17/34* (2006.01)

(52) U.S. Cl. ........................................ 606/185

(58) Field of Classification Search .......... 606/167–185; 604/164.01, 164.06, 164.08, 264, 506, 192
See application file for complete search history.

(56) References Cited

U.S. PATENT DOCUMENTS

| | | | | |
|---|---|---|---|---|
| 3,372,481 A * | 3/1968 | Skinner | | 30/210 |
| 4,157,086 A * | 6/1979 | Maiorano et al. | | 600/369 |
| 4,601,710 A | 7/1986 | Moll | | |
| 5,232,451 A | 8/1993 | Freitas | | |
| 5,254,128 A * | 10/1993 | Mesa | | 606/167 |
| 5,275,583 A * | 1/1994 | Crainich | | 604/264 |
| 5,314,417 A * | 5/1994 | Stephens et al. | | 604/264 |
| 5,364,372 A | 11/1994 | Danks | | |
| 5,417,705 A * | 5/1995 | Haber et al. | | 606/185 |
| 5,607,440 A * | 3/1997 | Danks et al. | | 606/185 |
| 5,609,604 A * | 3/1997 | Schwemberger et al. | | 606/185 |
| 5,611,780 A | 3/1997 | Decarie | | |
| 5,690,663 A * | 11/1997 | Stephens | | 606/185 |
| 5,797,943 A | 8/1998 | Danks | | |
| 5,868,773 A | 2/1999 | Danks | | |
| 5,882,340 A | 3/1999 | Yoon | | |
| 5,904,699 A | 5/1999 | Schwemberger | | |
| 5,916,232 A * | 6/1999 | Hart | | 606/185 |
| 6,017,356 A * | 1/2000 | Frederick et al. | | 606/185 |
| 6,063,099 A | 5/2000 | Danks | | |
| 6,238,407 B1 | 5/2001 | Wolf | | |
| 6,270,484 B1 * | 8/2001 | Yoon | | 604/264 |
| 6,497,687 B1 | 12/2002 | Blanco | | |
| 6,613,063 B1 | 9/2003 | Hunsberger | | |

(Continued)

FOREIGN PATENT DOCUMENTS

EP 0552851 A2 7/1993

(Continued)

*Primary Examiner* — Kathleen Sonnett
(74) *Attorney, Agent, or Firm* — DuBois, Bryant & Campbell, LLP; William D. Wiese

(57) ABSTRACT

An obturator has an elongated shaft with a first shaft portion and a second shaft portion within an obturator housing. The distal end of the first shaft portion creates a first shield and the distal end of the second shaft portion creates a second shield. A blade having a piercing tip and cutting edges is interposed between the first shield and the second shield. In use, once the piercing tip passes the body wall, the first shield moves to cover the piercing tip and protect internal organs from accidental injury while the cutting edges continue to cut the body wall. Once the second shield passes through the body wall, the second shield moves to cover the cutting edges.

15 Claims, 7 Drawing Sheets

U.S. PATENT DOCUMENTS

| | | |
|---|---|---|
| 6,716,201 B2 | 4/2004 | Blanco |
| 6,719,746 B2 | 4/2004 | Blanco |
| 6,835,201 B2 * | 12/2004 | O'Heeron et al. ............ 606/184 |
| 6,837,874 B1 * | 1/2005 | Popov ....................... 604/164.06 |
| 2007/0010842 A1 * | 1/2007 | Popov ........................... 606/185 |

FOREIGN PATENT DOCUMENTS

| | | |
|---|---|---|
| EP | 0608854 A2 | 8/1994 |
| WO | WO-94/09712 | 5/1994 |

* cited by examiner

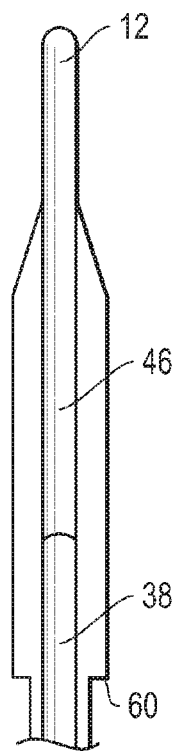
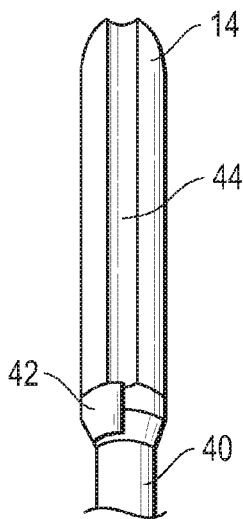
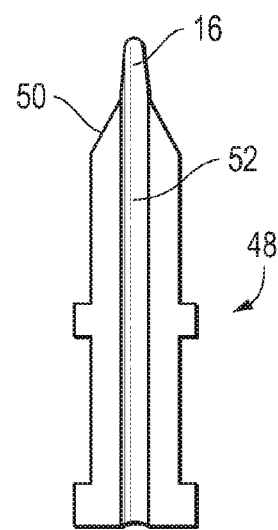
FIG. 4A
FIG. 4B
FIG. 4C
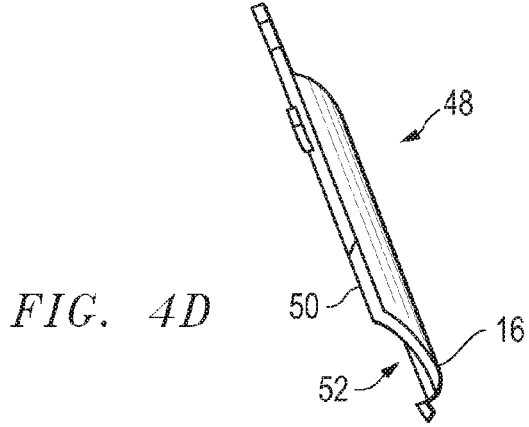
FIG. 4D
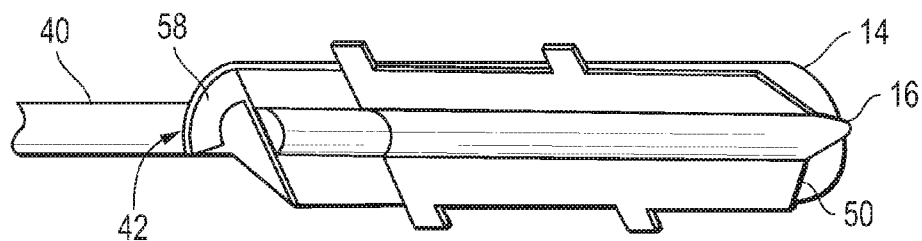
FIG. 5

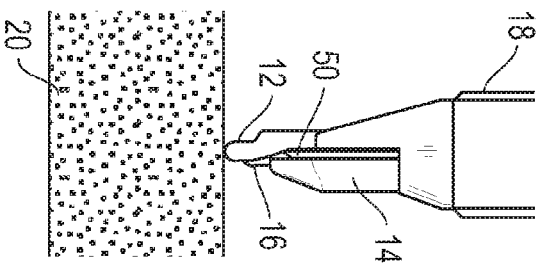
FIG. 6A
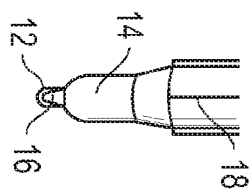
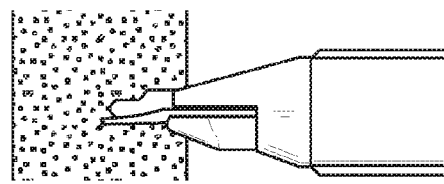
FIG. 6B
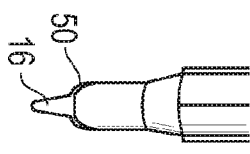
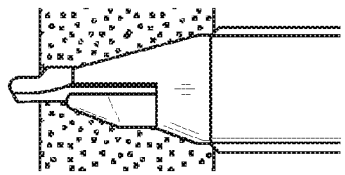
FIG. 6C
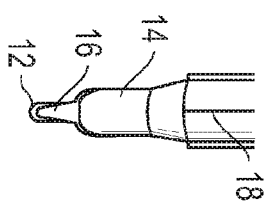
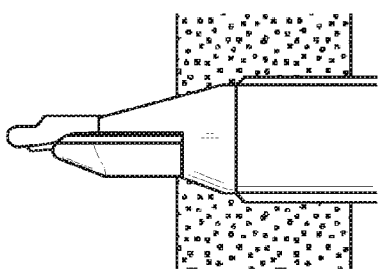
FIG. 6D
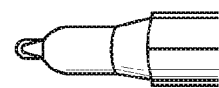

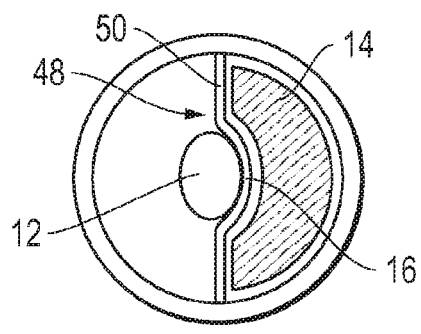
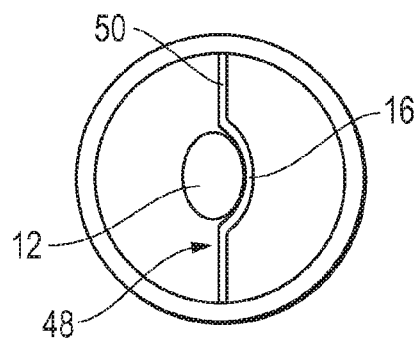
*FIG. 7A*  *FIG. 7B*
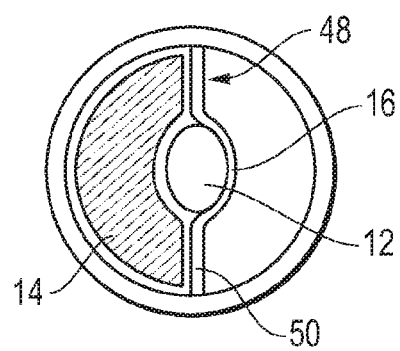
*FIG. 7C*
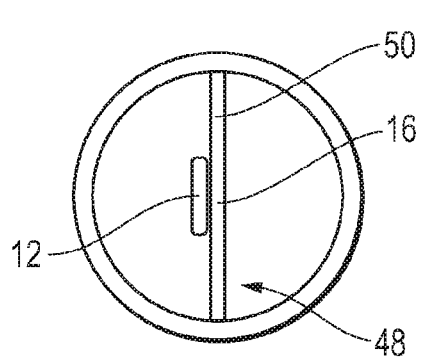
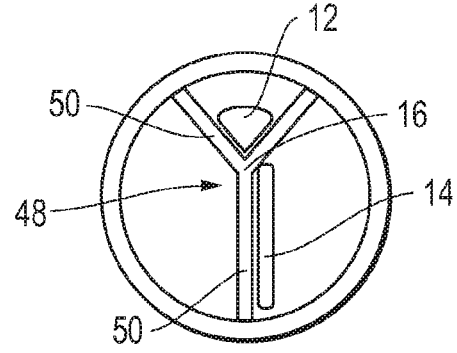
*FIG. 7D*  *FIG. 7E*

SURGICAL OBTURATOR

PRIORITY STATEMENT UNDER 35 U.S.C. §119 & 37 C.F.R. §1.78

This non-provisional application claims priority based upon prior U.S. Provisional Patent Application Ser. No. 60/549,199 filed Mar. 2, 2004 in the name of Michael T. Patton, entitled "Surgical Obturator," the disclosure of which is incorporated herein by reference.

TECHNICAL FIELD OF THE INVENTION

The present invention relates to a surgical instrument commonly referred to as a trocar, often used in laparoscopic surgery. More particularly, the invention relates to a trocar that includes an improved tip with one or more independently biased shields for facilitating the safe and efficient entry of the trocar through the body wall and into the body cavity of a patient.

BACKGROUND OF THE INVENTION

Laparoscopy is a minimally invasive surgical procedure that utilizes a small tubular laparoscope, or camera, to view a patient's internal organs. During laparoscopy, trocars are used to puncture the body wall, such as the abdominal wall, to provide access for the camera and thin laparoscopic surgical instruments. Since the incisions in these types of procedures are smaller than with conventional surgery, there is less patient trauma and reduced hospitalization. As a result, laparoscopy continues to grow in popularity.

A trocar assembly generally includes two major components, an obturator and a cannula. The obturator typically includes an elongate body having a sharpened distal tip. The sharp distal tip pierces and cuts the tissue forming the body wall. The cannula generally has a cylindrical configuration and a seal-valve housing. As the trocar is pushed or otherwise moved through the body wall, the sharp distal tip of the obturator functions to cut the tissue and provide an opening for the trocar. Once the trocar is operatively positioned, the obturator can be removed leaving the cannula to provide working access into the body cavity. For example, a laparoscope may be inserted through the cannula to view the body cavity or surgical instruments may be inserted through the cannula to perform ligations or other procedures.

Many surgical procedures are now being performed with the use of trocars. Originally these devices were used for cutting an opening into the body wall to insert and leave a drain tube. Previously these procedures required incisions of many inches. By minimizing the incision length, the stress and loss of blood suffered by patients is minimized and the recovery times of patients can be significantly reduced.

Initial entry into the abdominal cavity is inherently dangerous. The primary trocar insertion is commonly known as "blind entry" because the surgeon is unable to see the internal organs of the patient. Surgeons must take extreme caution to avoid potentially fatal injuries to internal organs and major vessels. Secondary trocar insertions are less dangerous because surgeons have the ability to inspect the body cavity and guide the positioning of the remaining trocars using the laparoscope inserted through the primary opening. However, significant injuries, and even fatalities, caused by secondary obturator cutting tips still occur.

It has been found that a relatively large force is required to push the sharpened tip of an obturator through the body wall. Once the sharpened tip penetrates the body wall, an opening is created by the lateral portions of the blade that permits the trocar to pass into the body cavity. Once the opening is sufficiently large to permit the full diameter of the obturator to pass through, resistance to penetration is removed and the obturator is free to move unrestricted into the body cavity. This sudden drop in resistance when the obturator passes into the cavity is sometimes called the "plunge effect." In most cases, delicate internal organs are very close to the inside of the body wall being pierced. Most laparoscopic penetrations are only performed after the internal cavity is filled with carbon dioxide, thereby expanding the body wall away from the internal organs, to minimize the danger of accidental injury due to the obturator coming into contact with internal organs. In most cases, however, the force required for penetration and the elastic nature of the body wall cause a severe depression where the trocar is entering the body cavity, thereby bringing the penetrating tip of the instrument closer to the internal organs. Failure to stop this cutting action after the inevitable sudden resistance drop can result in considerable damage to interior organs and other tissues within the cavity.

In an effort to avert these dangers to the patient, trocars have been developed with a variety of safety features and devices. One of the major areas of interest has been in attempting to provide an automatic safety shield to surround and protect the trocar tip immediately upon entry into the body cavity. In a typical configuration, the safety shield is shaped to cover the piercing tip and cutting portions of the blade. In one position, the shield is locked in place so that it covers the piercing tip and the blade. In a second position, the shield is unlocked but is biased in such a manner that, when the shield is not encountering pressure along its lateral axis the shield covers the blade. As the shield encounters pressure along its lateral axis, such as when the trocar is being pushed through a body wall, the shield retracts, thereby exposing the piercing tip and cutting edges of the blade. Once the full width of the blade has cut the body wall to the full diameter of the trocar, the pressure exerted on the shield is eliminated and the shield moves forward to cover the blade and locks in place. The locked shield is intended to protect internal body organs from incidental contact with the piercing tip and injury resulting therefrom. Trocars including various safety shield designs are illustrated in U.S. Pat. No. 4,535,773 issued Aug. 29, 1985 to Yoon, U.S. Pat. No. 4,601,710 issued Jul. 22, 1986 to Moll, U.S. Pat. No. 4,654,030 issued Mar. 31, 1987 to Moll et al, U.S. Pat. No. 6,613,063 issued Sep. 2, 2003 to Hunsberger, U.S. Pat. No. 5,916,232 issued Jun. 29, 1999 to Hart, U.S. Pat. No. 6,497,687 issued Dec. 24, 2002 to Blanco and U.S. Pat. No. 6,063,099 issued May 16, 2000 to Danks, et. al. Although these existing patents disclose improvements over previous trocar devices, they continue to be plagued with a number of problems. In fact, studies have shown that shielded obturators actually offer little or no protection to internal organs or vessels. As the resistance on the trocar drops as the trocar passes through the body wall, the spring-loaded shields do not travel fast enough to cover the cutting tip before the cutting tip comes in contact with internal organs.

Because the shield width on current shielded obturators extends close to the full diameter of the obturator, in some cases abutting the inside diameter of the cannula, the drop in tissue resistance on the shield and its surrounding cannula is virtually simultaneous. Thus, the shield simply cannot travel the distance to cover the cutting portion of the obturator in time to have a protective effect. Furthermore, because current shields have so much surface area, they actually contribute to the resistance force that leads to the dangerous plunge effect. For example, the shielded trocar disclosed in U.S. Pat. No.

5,709,671 utilizes a cutting blade with a diameter that is smaller than the obturator and a single shield configuration that extends to the full diameter of the obturator. In an effort to reduce the wound produced by the trocar, this design unfortunately increases the delay in shield deployment because abdominal wall tissue resists the shield until the full diameter of the cannula penetrates the cavity.

In another common shielded trocar configuration, the safety shield is essentially a tube that surrounds the obturator tip. Even though such a shield is effective in protecting the obturator tip (after the plunge effect), when these units are inserted through the body wall, the tissue surrounding the tubular safety shield offers significant resistance and impedes shield activation. As a result, the entire obturator tip and the shield must be fully inserted into the body cavity before the shield can activate. If extreme care is not exercised, the plunge effect may cause serious internal injury in the instant before the safety shield can achieve a fully extended position. In addition, trocars having these spring-loaded tubular safety shields require larger incisions. Particularly, the incision formed by the obturator generally must extend to the outer diameter of the tubular shield before the resistance of the body wall pressure is decreased to allow the shield to spring forward. It is also not uncommon for these tubular shields to possess a relatively large mass such that considerable time is required to move the shield into the distal or safety position.

U.S. Pat. No. 6,613,063 also describes a shielded obturator with a cutting portion that has a diameter less than the full diameter of the obturator. However, while the '671 shield extends to the full diameter, the '063 shield is significantly smaller than the obturator diameter. Although this design will likely allow the shield to cover the cutting area before the obturator completely enters the abdomen, it will certainly increase the force required to enter the abdomen. In this manner, the obturator described in this invention will function similar to a "blunt" obturator. This can happen for two reasons. First, since the shield has reduced surface area contacting the abdominal wall tissue, it will have a tendency to cover the cutting area if there is not constant resistance on it throughout the trocar insertion. Once the shield covers the cutting area, it locks into place and functions as a blunt obturator. If the surgeon recognizes that the shield has locked, he must stop the insertion, rearm the device, and begin again. Second, even if the obturator functions properly and the shield locks once the cutting area has penetrated the abdominal wall, there will be significant resistance on the obturator during the remainder of the insertion because no cutting surface remains. If the '063 device is constructed with a wider blade, similar to other shielded obturators, it will have the same disadvantages, namely exposed blade entry and delayed shield firing.

U.S. Pat. No. 6,497,687 also describes a mechanism that is designed to allow a shield to cover the entire cutting portion before the full diameter of the obturator enters the body cavity. As with the '063 patent, the shield is designed to spring forward and lock once the cutting tip penetrates the peritoneum. As with current shielded obturators, the cutting surface extends to the full diameter and, therefore, it will likely be necessary for the full diameter of the cutting portion to enter the abdominal cavity before the shield is free to move forward. Also similar to the '063 patent and current shielded obturator designs, only one shield is responsible for covering the entire cutting area. Finally, similar to the '063 patent, the shield will contact less tissue upon insertion, thus any hesitation by the surgeon will cause the shield to prematurely fire and lock.

The majority of shielded obturators are designed with one shield to cover the entire cutting surface. One exception is U.S. Pat. No. 5,275,583. In this design, however, multiple independently moving shields actually function similar to a single shield: each shield is responsible for covering a multiple of intersecting blade surfaces. The design of a single shield to cover an entire cutting surface is less than optimal for at least two reasons. First, if the cutting area extends to the full diameter of the obturator (in an effort to create less force to penetrate the body wall), the single shields will spring forward too late to protect the internal organs from obturator tip. Second, if the cutting area is significantly less than the full diameter of the obturator (in an effort to have the shields cover the cutting tip as quickly as possible), the obturator may require excessive force to enter the body cavity. As mentioned previously, this latter scenario can occur if the shield fires prematurely due to any hesitation upon entry, and the surgeon continues to force the trocar into the patient when the shields are forward and locked. Additionally, if the cutting surface of the obturator tip is too small, even if the shields fire at the appropriate time (upon initial penetration of the peritoneum), excessive force will be required to insert the remaining diameter of the obturator.

In summary, shielded obturator designs have traditionally linked the diameter of the protective shields with the exact diameter of the cutting surface. It is important to note that inexperienced or less-skilled surgeons are the most likely to hesitate, even slightly during trocar insertion. Therefore, it is desirous to have a shielded obturator that not only provides ease of insertion, but also has a mechanism that reduces the chance for premature shield locking.

Another common obturator configuration includes a blade having a symmetrical triangular form. These blades tend to form an opening which results in a wound consisting of three cuts each radiating from a central puncture or penetration point. While it is generally agreed that this blade configuration provides a low entry force, the concern remains that the resulting wound can result in herniation, as well as other complications associated with wound closure and healing.

Other obturators have only a single flat blade. These obturators penetrate the body wall through a single incision which reduces the concerns about wound herniation, closure and healing. In many cases, however, this configuration also fails to provide an incision which accommodates the full diameter of the obturator. As a result, insertion forces required to penetrate the body wall tend to be relatively high. Additionally, forcing a cylindrical shaped trocar through a linear incision can actually result in the propagation of the wound.

Still other trocars on the market utilize blunt obturator tips to reduce the potential for accidental sharp injuries. Such a device is disclosed in U.S. Pat. No. 5,271,380. These devices are not as popular among surgeons because they require excessive force to enter the abdominal cavity. Additional force creates an even more dramatic plunge effect. Because this translates to greater loss of control, it is not surprising that blunt trocars have also been responsible for injuries, sometimes resulting in death. These devices were designed to separate tissue layers rather than cutting through them. Several similar designs have been introduced over the years, however each one exacerbates the plunge effect.

Another common feature to most shielded obturator designs is the locking mechanism. Most shields are designed to lock into place once they cover the entire cutting portion of the obturator. This locking mechanism is used to prevent the shield from being inadvertently retracted, thereby exposing the cutting portion, once the obturator has fully penetrated the body wall. In those cases when the shields prematurely fire and lock before entering the body cavity, various methods are used to unlock the shield and reset the locking mechanism. One problem with the '063 and '687 designs is that any significant decrease in shield diameter will likely cause the shield to prematurely move proximally to cover the cutting portion. This is especially troublesome during the primary insertion because premature locking could falsely indicate to the surgeon that the abdominal cavity has been penetrated. The surgeon may then remove the obturator only to realize that the insertion must be repeated. If the surgeon even slightly hesitates during insertion, the shields in the '063 and '687 patents would likely fire and lock. Optimally, the surgeon would stop penetration and press a lock release button to continue cutting. Multiple rearming of the shielded obturator to enter the body cavity can cause needless frustration. If the shield prematurely fires and the surgeon is unable to rearm the obturator, significant force to enter the abdomen would be required. Finally, problems can arise if the surgeon has entered the cavity, but does not realize it. For example, a surgeon that believes that the trocar is still in the body wall when it is actually resting on bowel could rearm the trocar and enter the bowel.

U.S. Pat. No. 6,063,099 describes a shielded obturator with two locking positions. The single shield is designed to first lock into position over the cutting tip before the entire obturator penetrates the abdomen. Since the lateral cutting edges remain exposed, the obturator should be allowed to finish cutting through the abdominal wall even if the shield is locked into the first position. Unfortunately, this obturator's shield design is similar to other shielded obturators in that only a single shield is responsible for covering the entire cutting area. Like the '687 patent, the shield described in the '099 patent has less distance to travel to cover the cutting tip, and thus will likely prematurely cover the cutting tip before entry into the body cavity. If it does not prematurely fire, it will still be delayed in covering the cutting tip like other shielded obturators. Thus the first locking position does not add any protection to the original single locking design. It is desirous to have a shielded obturator with a shield that locks before the plunge effect occurs. However, as has been previously discussed, it can be disadvantageous to have a shield that prematurely locks. It is commonly known that most trocars, whether sharp or blunt, will likely puncture bowel that has adhered to the inner body wall in the location of the trocar penetration. However, it is far more common to have bowel that loosely adheres to the body wall. In this case, shielded obturators can injure the bowel if the cutting tip precedes the shield, as occurs in most insertions. The double locking mechanism in the '099 patent offers no additional protection to bowel injuries, because, as with loosely adherent bowel, it is important only to have the cutting tip covered, not locked. Only a significant force against a spring-loaded shield will cause it to retract.

Another problem with existing trocar devices is that many employ complicated actuation and locking mechanisms requiring far too much expense and often necessitating costly mated trocar and cannula assemblies. With the current emphasis on cost controls in health care, it is desirable to have simple, lower cost instruments without sacrificing quality.

As can be seen from the foregoing discussion, trocars currently used for laparoscopic surgical procedures do little to prevent injuries to internal organs during insertion and manipulation of the trocar. Although a significant amount of effort has been expended in improving trocar designs, the results are still poor. Present procedures frequently injure internal organs, and the resulting wounds can be serious or even fatal. A need exists for safer trocars, especially given that laparoscopic surgical procedures are likely to become more commonplace in the future. Specifically, there is a need for a shielded obturator to have a shield mechanism that effectively covers the obturator's cutting tip before the plunge effect. It is also desirous to have a shield mechanism that prevents premature locking of the shield. There is also a need for a shielded obturator that reduces the chance of inadvertent injury to the bowel caused by an exposed cutting tip upon abdominal entry.

SUMMARY OF THE INVENTION

The present invention provides an improved trocar for use in a wide variety of surgical procedures and is intended for guarding against accidental puncture wounds of a patient when operatively entering the body cavity. It is generally directed towards a trocar that allows a surgeon to easily penetrate tissue covering a body cavity while providing protection for the piercing tip of the blade once it passes through the tissue. The trocar is generally configured with an obturator, having an obturator shaft within an obturator housing, fitted within a cannula. Once the body cavity wall is penetrated by the obturator, the obturator can be removed, leaving the cannula behind such that medical instruments may be inserted through the lumen of the cannula.

The obturator shaft is an elongated shaft comprised of a first shaft portion and a second shaft portion. The distal end of the first shaft portion creates a first shield and the distal end of the second shaft portion creates a second shield. A blade is interposed between the first shield and the second shield. The blade has a piercing tip and cutting edges. The first shield is shaped and biased to cover the piercing tip but not the cutting edges and the second shield is shaped and biased to cover the cutting edges. Although the preferred embodiment shows the shields on either side of the blade, the first shield and second shield may be oriented with respect to the blade in any combination. For example, the first shield may be located on one side of the blade and the second shield may be located on the other side. In another configuration, the first shield and the second shield may be located on the same side of the blade and a tissue expander may be located on the other side.

A latching mechanism is configured to prevent the second shaft portion, and thereby the second shield, from moving proximally. An actuating mechanism releases the latching mechanism so that the second shaft portion can move proximally and expose the cutting edges and the first shaft portion can move proximally and expose the piercing tip, thereby moving the obturator into the cutting position. The second shaft portion is configured with a second shield stop. When the second shaft portion is latched into its distalmost position by the latching mechanism, the second shield stop prevents the first shield from moving proximally to expose the piercing tip. Consequently, the first shield is biased distally but does not lock immediately after it covers the piercing tip. Once the piercing tip passes the body wall, the first shield is free to cover the piercing tip and protect internal structures from accidental injury while the cutting edges continue to cut the body wall. Since the first shield covers the piercing tip immediately after tip entry, protection of the piercing tip is provided at the time of the initial entry and prior to the plunge effect. The cutting edges, however remain exposed and allow for full insertion into the cavity. Once the second shield passes through the body wall it distally moves to cover the cutting edges and is latched into place by the latching mechanism. Through the action of the second shield stop, the first shield is also locked into place and prevented from moving proximally. The second shield locks into place and, subsequently, the first shield locks, before the obturator's full diameter penetrates the body wall.

This invention, together with the additional features and advantages thereof will become more apparent to those of skill in the art upon reading the description of the preferred embodiments, with reference to the following drawings.

DESCRIPTION OF THE DRAWINGS

A better understanding of the system and method of the present invention may be had by reference to the drawing figures, wherein:

FIG. 4A is a side view of the first shield;

FIG. 4B is a side view of the second shield;

FIG. 4C is a bottom view of the blade;

FIG. 4D is an isometric view of the blade;

FIG. 5 is a bottom view of the second shield coupled with the blade;

FIGS. 6A through 6D show, in sequential diagrammatic sectional views, the obturator of the present invention penetrating the body wall; and FIGS. 7A through 7E shows the distal end of the obturator with alternative blade and shield configurations.

DESCRIPTION OF TILE PREFERRED EMBODIMENTS

The present invention is an improved trocar for use in creating an incision in a patient and establishing an orifice for further medical procedures. It should be appreciated that the present invention is equally applicable to any appropriate surgical procedure. References to surgical procedures and other terms used herein may be applicable to medical and veterinary surgery as well as other non-medical applications.

Figure 1:
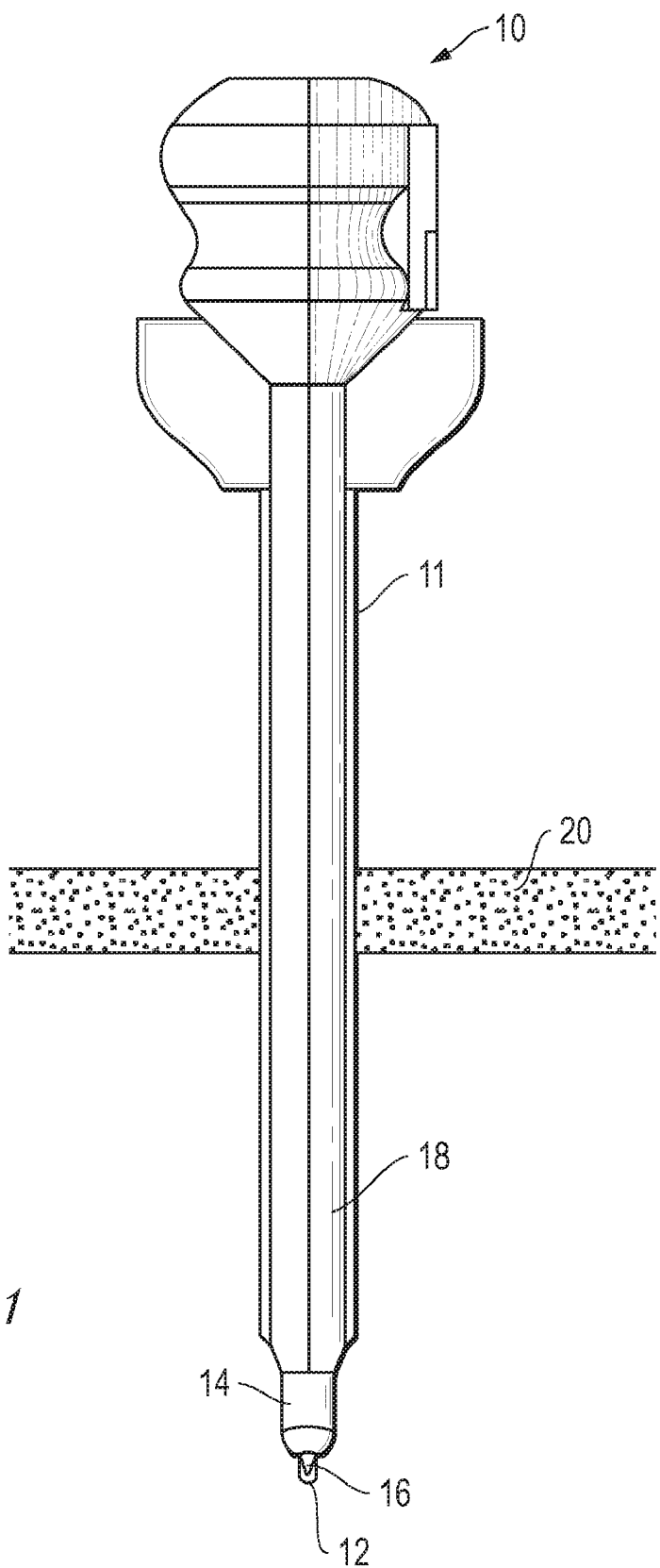
FIG. 1 is a side view of the obturator of the present invention, fitted within a cannula, shown piercing a body wall.

Referring now to the various figures of the drawing wherein like reference characters refer to like parts throughout the several views. FIG. 1 shows an improved obturator 10 in accordance with one preferred embodiment of the present invention. In this view, the obturator 10 is fitted within a cannula 11. At the distal end of the obturator 10 is a piercing tip 16, a first shield 12 and a second shield 14, with both the first shield 12 and the second shield 14 shown in their distalmost positions. The obturator 10 is first inserted through the cannula 11, thereby creating a trocar, before being inserted through the body wall 20, such as an abdominal body wall. The obturator 10 is then pressed against the body wall 20, whereby the obturator 10 creates an incision in the body wall 20. The piercing tip 16 initiates the incision into the body wall 20, through which the obturator 10 and the cannula are permitted to penetrate into the body cavity. Once the obturator 10 and the cannula have penetrated into the body cavity, the obturator 10 can be removed, leaving the cannula 11 in place. The surgeon then has unfettered access through the body wall 20 and into the body cavity through the lumen of the cannula 11.

The obturator housing 18 is generally cylindrical having a circular cross section, although cross sections of different shapes may be advantageous at times. In addition, it is not necessary for the entire obturator 10 or the obturator shaft 30 to have a consistent cross section, either in shape or in radial sizes, along its axis. However, the generally circular cross section of the obturator housing 18 may be advantageous when passing the obturator housing 18 through the cannula 20.

Figure 2A:
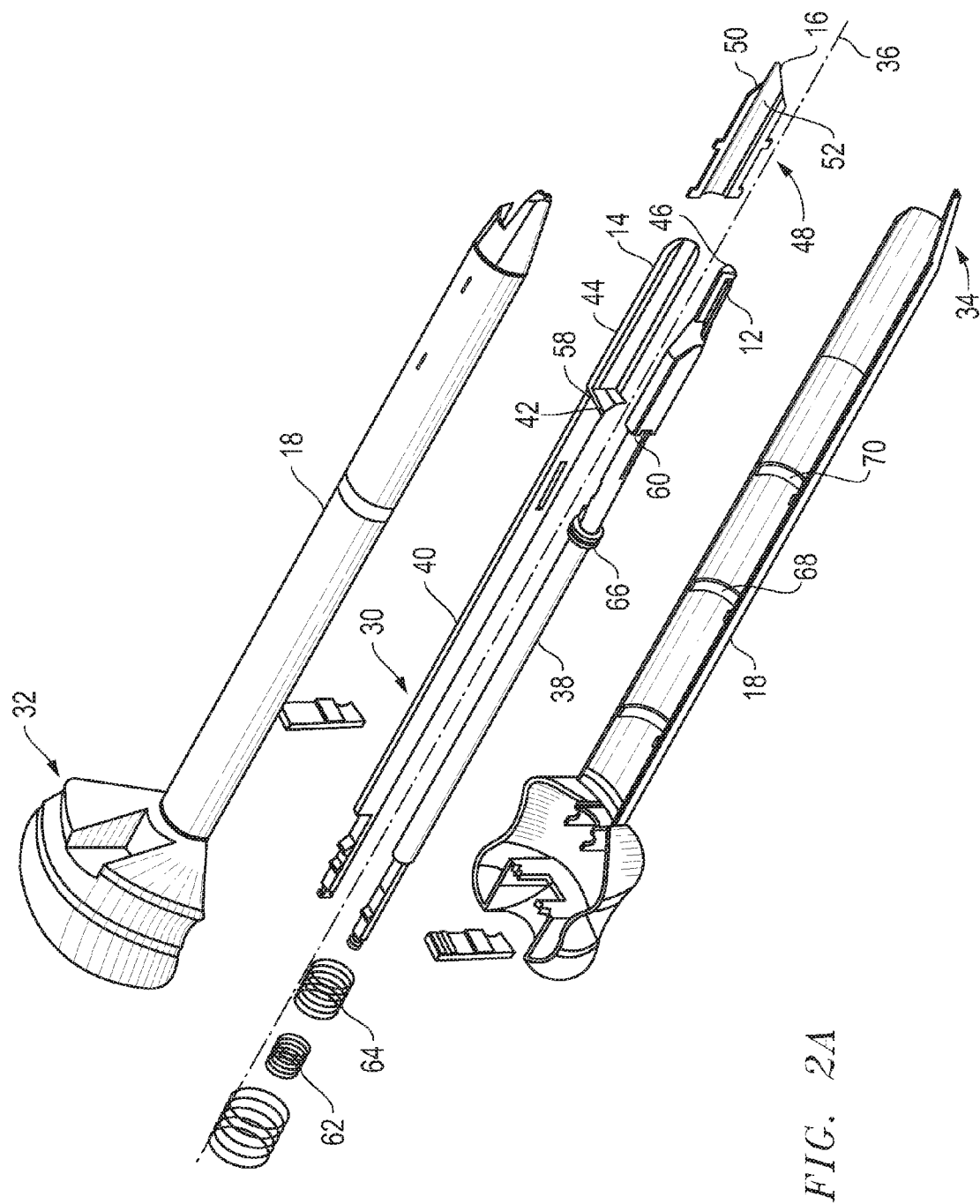
FIG. 2A is an exploded view of the obturator.

FIG. 2A shows an exploded view of an obturator shaft 30, which is located within the shaft housing 18, extending between a proximal end 32 and a distal end 34 along a longitudinal axis 36. The obturator shaft 30 includes a first shaft portion 38 and a generally opposing second shaft portion 40. Second sleeve ring 42 attached to the second shaft portion 40 functions to keep the first shaft portion 38 from separating from the second shaft portion 40, although other methods and apparatus may serve a similar function, and the inner surface of the cylindrical housing 18 further assists in maintaining the portions 38 and 40 in an opposing relationship. The proximal face of the second sleeve ring 42 also serves as a second shield stop 58.

Figure 2B:
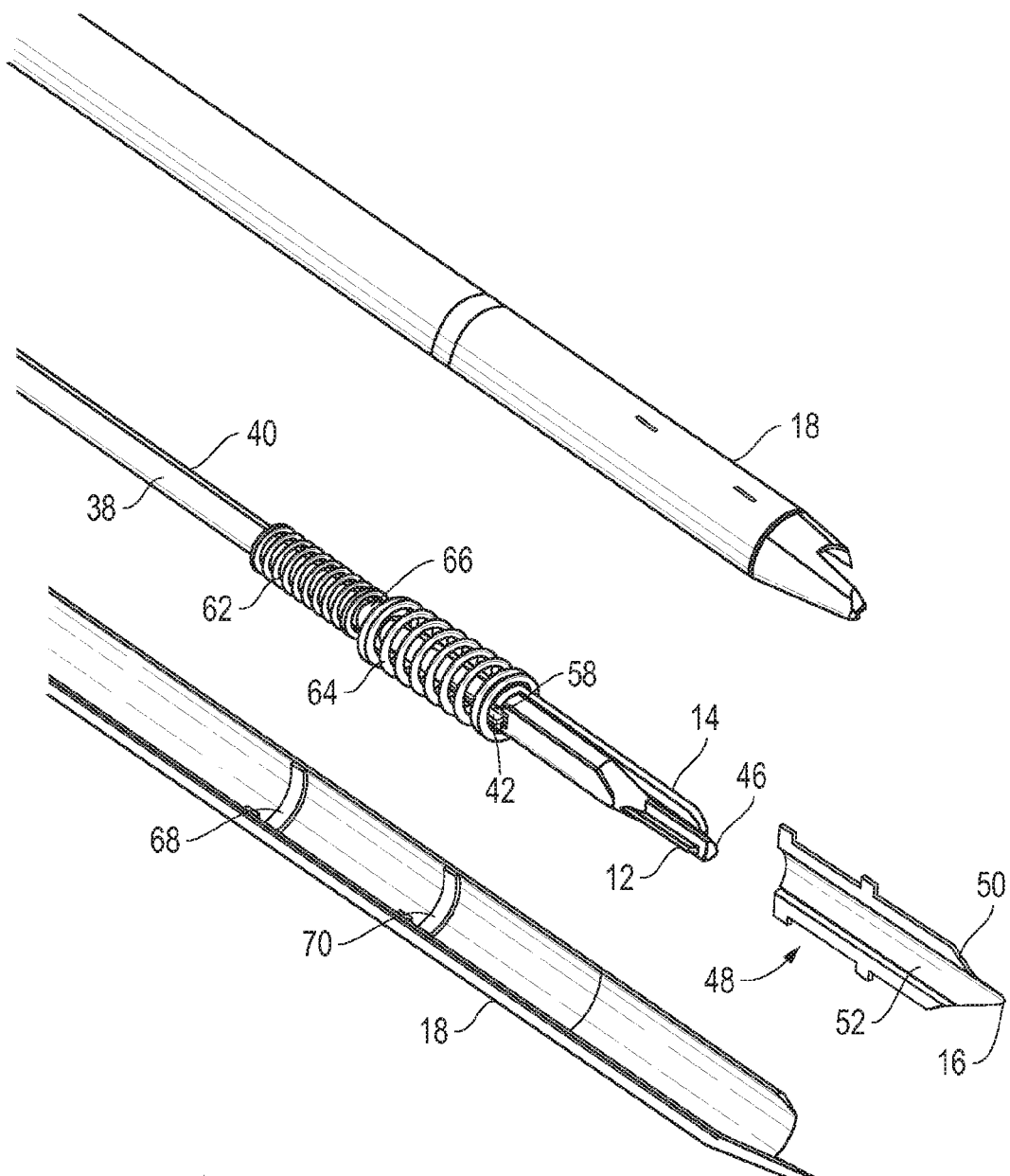
FIG. 2B is an exploded view of the distal end of the obturator.

FIG. 2B shows an exploded view of the distal end of the obturator shaft 30 in which the first shaft portion 38 extends along the longitudinal axis 36 and terminates at the distal end 34 to form a first shield 12. The second shaft portion 40 extends along the longitudinal axis 36 and terminates at the distal end 34 to form a second shield 14. The second shield 14 preferably has a rounded distal end, but may be any configuration that is generally blunt. A blade 48 is positioned between the first shield 12 and the second shield 14 and is secured to the housing 18 near its distal end. In one embodiment, the first shield 12 is biased by a first biasing element 62 along the longitudinal axis 36 to cover the piercing tip 16 and the second shield 14 is biased by a second biasing element 64 along the longitudinal axis 36 to cover the cutting edges 50. The first biasing element 62 is coupled to the first sleeve ring 66 and the first housing block 68 for biasing the first tip portion 12 into its distalmost position. The second biasing element 64 is coupled to the second sleeve ring 42 and the second housing block 70 for biasing the second tip portion 14 into its distalmost position.

The first biasing element 62 and the second biasing element 64 may be, for example, helical springs. When the first tip portion 12 is in its distalmost position, the spring 62 may be in compression so as to maintain a constant distal pressure on the first tip portion 12. When the first tip portion 12 encounters resistance, such as when penetrating the body wall 20, the first tip portion 12 is moved proximally and the spring 62 is further compressed. This compression results in additional force being applied against the first tip portion 12, thereby urging the first tip portion 12 distally. It may be advantageous to utilize a biasing element with a stronger force, such as a spring with a stronger spring force, for the first biasing element 62 so that the first tip portion 12 is more strongly biased than the second tip portion 14. A stronger first biasing element 62 provides a quicker transition from the point at which the piercing tip 16 is uncovered to the point at which the piercing tip 16 is covered by the first shield portion 12. Of course, the benefit of utilizing a stronger first biasing element 62 should not exceed the point at which the pressure exerted by the first biasing element 62 is greater than the resistance encountered when using the obturator such that the first biasing element 62 prevents the first tip portion 12 from moving proximally.

The second biasing element 64 functions similarly to the first biasing element 62. That is, when the second tip portion 14 is in its distalmost position, the spring 64 may be in compression so as to maintain a constant distal pressure on the second tip portion 14. When the second tip portion 14 encounters resistance, such as when penetrating the body wall 20, the second tip portion 14 is moved proximally and the spring 64 is further compressed. This compression results in additional force being applied against the second tip portion 14, thereby urging the second tip portion 14 distally.

Figure 3:
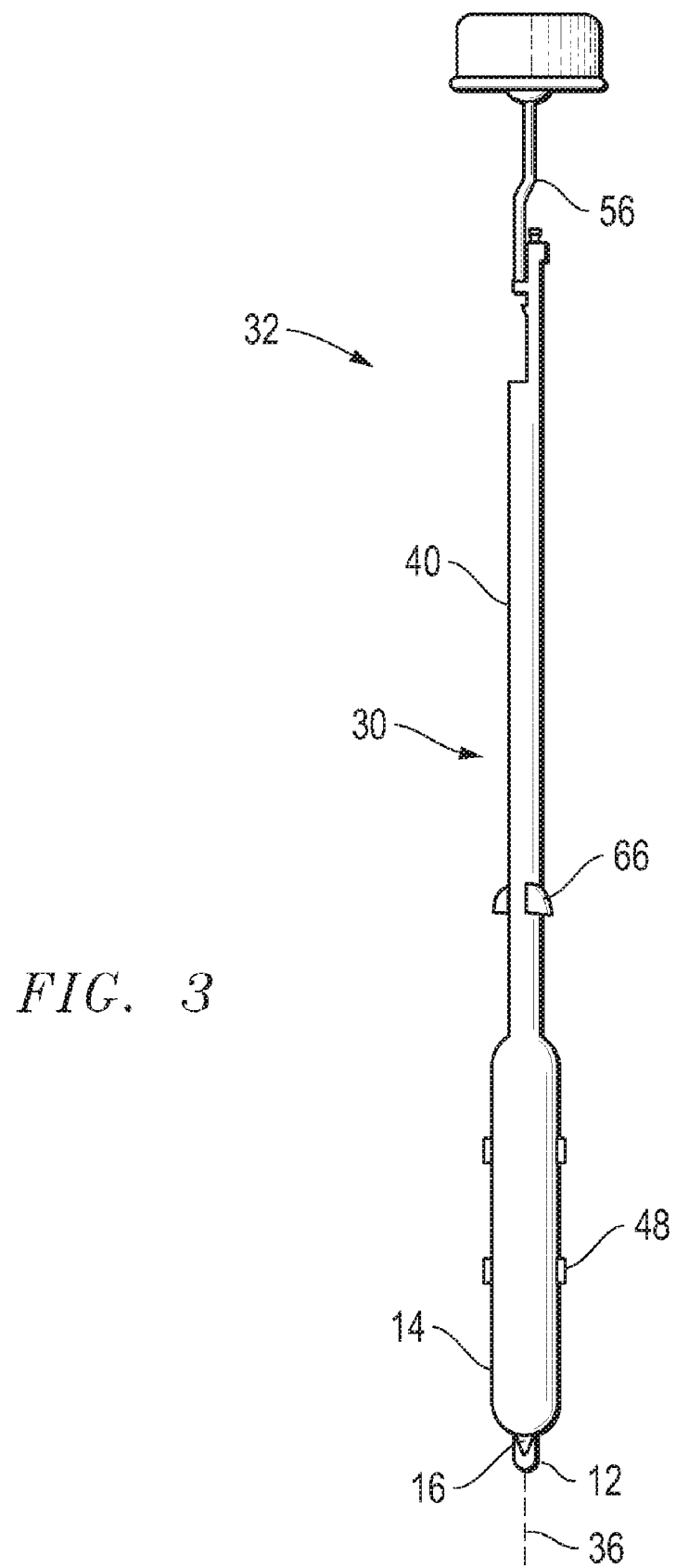
FIG. 3 is a disassembled side view of the obturator shaft.

FIG. 3 shows a view of an assembled obturator shaft 30. The first shaft portion 38 and the second shaft portion 40 may be configured to move relative to one another along the longitudinal axis 36 without radial separation.

FIG. 4A shows the distal end of the first shaft portion 38 and FIG. 4B shows the distal end of the second shaft portion 40. The first shaft portion 38 is configured to be longitudinally moveable relative to the second shaft portion 40. The inner surfaces of the first shaft portion 38 and the second shaft portion 40, other than the respective distal ends 34, may be configured with opposing planar sections along the depth of the shaft 30 aligned with the longitudinal axis 36 such that the inner surfaces on each of the shaft portions slide against one another along the longitudinal axis 36.

The distal end of the first shaft portion, shown in FIG. 4A as the first shield 12, is configured with a semi-circular protrusion 46 and the distal end 34 of the second shaft portion 40, shown in FIG. 4B as the second shield 14, is configured with a semi-circular groove 44. The first shield 12, the blade 48 and the second shield 14 are configured so that the semi-circular protrusion 46 of the first shield 12 juxtaposes within groove 52 of blade 48, which juxtaposes within semi-circular groove 44 in the second shield 14. The semi-circular protrusion 46 and the groove 52 of blade 48 are configured so as to be in slidable contact with one another along the longitudinal axis 36. Similarly, the groove 52 of blade 48 and semi-circular groove 44 are configured so as to be in slidable contact with one another along the longitudinal axis 36. The shape of the first shield 12 has a circular cross section and blunt end but other cross sections may also be advantageous Referring now to FIG. 4C and FIG. 4D showing the blade 48 including a piercing tip 16 and cutting edges 50, the piercing tip 16 has a cutting surface defined by a first acute angle when measured from the longitudinal axis, and the cutting edges 50 have a cutting surface defined by a second acute angle when measured from the longitudinal axis that is greater than the first acute angle. The blade 48 is attached to the housing 18 and is positioned between the distal end 34 of the first shaft portion 38 and the distal end of the second shaft portion 40 such that each of the distal end 34 of the first shaft portion 38 and the distal end of the second shaft portion 40 are slidable moveable with respect to the blade 48 such that the first shield 12 of the first shaft portion 38 can be distally extended to cover the piercing tip 16 of the blade 48 and the second shield 14 of the second shaft portion 40 can be distally extended to cover the cutting edges 50. The blade 48 is configured with a groove 52 along its longitudinal axis having a diameter that is approximately one-half the width of the blade 48. The groove 52 extends to and includes the tip 16 but does not include the cutting edges 50 which are flat. A protrusion formed by the groove 52 on the opposite side of the blade 48 juxtaposes in the groove 44 of the second shield 14 and the protrusion 46 of the first shield 12 juxtaposes in the groove 52 of the blade 48. The piercing tip 16 and the cutting edges 50 are sharpened along their edges and may be for example, serrated along the piercing tip, the cutting edges, or both. The blade 48 can be made out of a variety of materials, including metal, plastic, or like materials.

The configuration of the blade 48 presents several distinct advantages over existing trocars. First, because the blade 48 is configured with a groove 52 to carry the first shield 12, the shield that covers the piercing tip 16 is at all times in close proximity to the piercing tip 16. It is advantageous to have the first shield 12 reside in the center of the blade 48 since it will be the first part of the cutting tip to enter the body cavity. Second, the configuration of the rounded piercing tip 16 around the groove 52 or the inclusion of serrated edges on one or more portions of the piercing tip 16 or the cutting edges 50 is designed to allow the obturator to enter the inner layer of body wall 20 tissue (e.g., peritoneum) with greater ease than traditional obturator cutting tips. This results in less "tenting", or angling of the obturator tip and tissue towards vital internal organs. Tenting, as seen with blunt trocars, reduces the critical distance between the piercing tip 16 and internal organs, thus similarly reducing the time for a shield to cover the piercing tip 16. Third, the semicircular shape provides the piercing tip 16 with greater cutting surface area than standard flat blade obturators, thereby offering a smoother, and thus more controlled, entry into the body cavity. Fourth, because many surgeons instinctively turn their wrists while inserting the trocar, the partially curved piercing tip 16 may cause less trauma to the tissue than traditional flat or pyramidal-shaped blades.

Referring now back to FIG. 3, in one embodiment an actuating mechanism 56 is provided at a proximal end of the shaft 30 and includes a button that, when pressed, arms the obturator 10 by moving the distal tip of the button over a ramp, allowing a cam lock on the proximal end of the obturator 10, called the shield lock, to pass under the obturator housing hinge or hinges and thereby allowing the first and second shields to retract in response to pressure exerted by the body wall 20 during entry of the obturator tip. The actuating mechanism 56 may be a button, a trigger or a similar device at the proximal end of the obturator housing 18 and coupled with the latching mechanism. A first biasing element 62 and a second biasing element 64 are operably mounted to the first shield 12 and the second shield 14 to bias the shields into their distalmost position but allow for retraction during entry into the body wall 20.

Thus, following arming and with the beginning of tissue insertion, the first shield 12 retracts longitudinally in the channel along the blade 48 from a position in which the piercing tip 16 is covered to a position where it is exposed to allow for tissue cutting to begin As the trocar is further inserted into the body, the second shield 14 also retracts longitudinally along the surface of the blade 48 from a position in which the cutting edges 50 are covered to a position where the cutting edges 50 are exposed to allow for continued tissue cutting.

At such time as the first shield 12 no longer encounters resistance during the cutting process, for example, when the piercing tip 16 begins its entry through the body wall, tissue resistance against the shield drops and the first shield 12 is biased back to its extended position covering the piercing tip 16. At such time as the second shield 14 no longer encounters resistance during the cutting process, for example, when then second cutting edges 50 have almost penetrated through the body wall, tissue resistance against the shield drops and the second is biased back to its extended position covering the cutting edges 50.

As the second shield 14 returns to is extended position, the shield lock passes under the hinge or hinges, and the shield lock reverts to its original locking position which abuts the hinge or hinges, preventing the second shield 14 from being able to be retracted. The first shield 12 and second shield 14 are operably connected together such that the first shield 12 is prevented from retracting unless the second shield 14 is allowed by the shield lock to retract. This prevents the first shield 12 from moving proximally and retracting past the point at which the piercing tip 16 is exposed.

In one embodiment of the invention, the obturator has only a first shield 12 that provides protection for the piercing tip 16 but at all times leaves the cutting edges 50 exposed. Such a configuration may be useful, for example, as a secondary trocar when a surgeon has previously penetrated the abdominal cavity and inserted a camera, thereby having the ability to visually observe the entry of the trocar on subsequent insertions. This construction could reduce the number of parts in the trocar, thereby reducing the cost of the device. In this embodiment, the first shield 12 protects against the sharpened piercing tip 16 coming into contact with tissue or other materials inadvertently but allows the cutting edges 50 to cut through tissue. In the cutting position, the first shield 12 is able to slide proximally from its distalmost position along the longitudinal axis 36, thereby exposing the piercing tip 16. In this embodiment, the first shield 12 could be locked in its distalmost position by a latching mechanism once the obturator has penetrated the body wall 20 to a known degree, or could have no locking mechanism at all.

Referring now to FIG. 5 which shows the distal end 34 of the second shaft portion 40 and blade 16, it will be noted that the second shaft portion 40 is configured with a second shield stop 58. When the second shaft portion 40 is latched into its distalmost position by the latching mechanism, the second shield stop 58 abuts the shoulder 60 of the first tip portion 12, thereby preventing the first shield 12 from moving proximally past the second shield stop 58. Consequently, the first shield 12 is biased distally but does not lock immediately after it covers the piercing tip 16 unless the first shield 12 and the second shield 14 move to their distalmost positions simultaneously. Once the piercing tip 16 begins to penetrate the inner abdominal wall, the first shield 12 is free to cover the piercing tip 16 and protect internal structures from accidental injury while the obturator continues to penetrate the body wall 20. Since the first shield 12 covers the piercing tip 16 immediately, it immediately transforms the distal end 34 from a sharp piercing tip to a blunt protective tip. Once the second shield 14 passes through the body wall 20 and is latched into place by the latching mechanism, the first shield 12 is also locked into place and prevented from moving proximally by the second shield stop 58. This locked position prevents both shields from retracting even if static structures are contacted during the plunge effect.

In use, the first shield 12 is retracted to expose the piercing tip 16, either manually or by pressure produced by the body wall 20 as the obturator is inserted through the body wall 20. The first shield 12 is biased to cover the piercing tip 16 when there is reduced pressure exerted on it by the body wall 20. Ideally, the first shield 12 covers the piercing tip 16 as soon as the piercing tip 16 passes through the body wall 20. The first shield 12 may actually precede the piercing tip 16 into the cavity if the biasing force is greater than the resisting force offered by the remaining tissue. This result has been demonstrated in animal studies where the obturator penetrates the body wall 20 but fails to puncture an inflated balloon that is pressed up against the tissue to simulate internal organs.

FIGS. 6A through 6D illustrate the obturator 10 and cannula 20 penetrating the body wall 20. In FIG. 6A, the first shield 12 and second shield 14 are in their distalmost positions. Once the actuating mechanism 56 releases the latching mechanism, both shields are free to move proximally thereby exposing piercing tip 16 and cutting edges 50. FIG. 6B shows both shields retracted as the obturator 10 and cannula penetrate the body wall 20. In FIG. 6C, the piercing tip 16 has penetrated the innermost layer of the body wall 20, and the first shield 12 has moved distally to cover the piercing tip 16. In FIG. 6D, the obturator 10 has penetrated the body wall to the point where the second shield 14, having no resistance placed on it by the body wall tissue, moves distally to cover the cutting edges 50. Once the second shield 14 moves into this distalmost position, the latching mechanism automatically locks it into place, preventing any proximal movement that would expose the cutting edges 50 unless the actuating mechanism is intentionally triggered. Since the first shield 12 abuts the second shield 14, it also is locked into place, which prevents any undesired proximal movement that would expose the piercing tip 16.

The present invention includes a number of other configurations of the blade and the shield or shields. For example, FIG. 7A shows the distal end of the obturator of the preferred embodiment in which the first shield 12 is located on the opposite side of the blade 48 as the second shield 14. FIG. 7B shows another embodiment in which the first shield 12 protects the piercing tip 16 but not the cutting edges 50. FIG. 7C shows an alternative embodiment in which the first shield 12 is located on the same side of the blade 48 as the second shield 14. FIG. 7D shows yet another embodiment in which the blade 48 is planar and the first shield 12 protects the tip of the blade but not the cutting edges. In another embodiment, as shown in FIG. 7E, the blade 48 has a pyramidal tip with the first shield 12 located between two portions of the blade and the second shield 14 located between a second two portions of the blade. Those skilled in the art will recognize that other configurations may provide additional advantages. For example, if a tissue expander is configured on the opposite side of the blade 48 as the first shield 12 and the second shield 14.

As previously described, in one embodiment, the first shield 12 is biased by a first biasing element 62 along the longitudinal axis 36 to cover the piercing tip 16 and the second shield 14 is biased by a second biasing element 64 along the longitudinal axis 36 to cover the cutting edges 50. When the obturator 10 is pressed against the body wall 20, the first shield 12 is biased distally by first biasing element 62, but free to move proximally in response to the pressure exerted on the first shield 12 by the body wall 20. Similarly, the second shield 14 is biased distally by the second biasing element 64, but free to move proximally in response to pressure exerted on the second shield 14 by the body wall 20. When the piercing tip 16 begins its initial entry into the body cavity, the first shield 12 is biased forward to protect the piercing tip 16 from contacting internal organs or vessels that may lie adjacent to the inner surface of the body wall 20. However, because the second shield 14 is independently biased, it remains free to move proximally to continue to expose the cutting edges 50 in response to pressure exerted by the body wall 20 on the second shield 14. When the obturator passes through the body wall 20, however, the pressure against the second shield 14 is released and it is biased forward to cover the cutting edges 50. Once the second shield 14 is locked in place, the first shield 12 is also locked in place, thereby preventing damage to internal organs by the piercing tip 16.

There are other ways to ensure that the first shield is locked into place before the plunge effect occurs. For example, the obturator may be configured with a moving part that engages once the obturator senses that the pressure exerted by the body wall 20 has dropped beyond a predetermined range. Another alternative is a carbon dioxide sensor that causes the first shield 12 to lock when the carbon dioxide inside the abdomen of a patient undergoing a laparoscopic procedure is detected.

Although it is important to ensure that the first shield 12 covers the piercing tip 16 before the plunge effect occurs, thereby protecting internal organs from sharp injury due to the exposed piercing tip 16, it is also important that the first shield 12 does not prematurely lock into place. Premature locking can occur if the surgeon disrupts the obturator penetration for any reason. Smaller shields have less surface area to contact tissue; thus, there is greater likelihood that any sudden hesitation in forward progression towards the body cavity will cause the shield to prematurely fire and lock. The obturator 10 will function as a "blunt" obturator unless the surgeon remembers to unlock the shields on the obturator and reinitiate penetration. Multiple premature locking occurrences can become a nuisance to the surgeon.

One novel feature of this invention is that the first shield 12 immediately covers the piercing tip 16 yet leaves the cutting edges 50 exposed. This allows the first shield 12 to protect the dangerous part of the obturator, the piercing tip 16, while allowing the obturator 10 to remain effective in entering the body cavity in a smooth and controlled manner. Traditional shielded obturators have single shields that are biased to cover both the cutting tip and cutting edges when the full diameter of the obturator, or at least the full diameter of the cutting edges, completely penetrates the body wall 20. Since these shields are designed to cover both the cutting tip and the cutting edges, the shields remain retracted, and the dangerous cutting tip remains exposed, during the entire entry process. This may result in the cutting tip causing injury to internal structures as the obturator penetrates the body cavity (e.g. loosely adherent bowel). Studies have shown that traditional spring-loaded shields cannot spring forward fast enough to adequately protect the internal organs.

It is a benefit of the present invention to provide a safer trocar for piercing body cavity walls.

It is a further benefit of the present invention to provide an improved trocar which includes an obturator piercing tip which is effective for piercing through body wall without tearing the tissue thereof.

It is also a benefit of the present invention to provide an improved shield design which will provide faster coverage of the piercing tip.

It is a further benefit of the present invention to provide an improved trocar which includes a protective shield which covers the trocar piercing tip upon passage of the tip into the body cavity, thereby protecting the patient from injury caused by the piercing tip.

It is a further benefit of the present invention to provide a trocar in which the piercing tip of the obturator blade is protected once it enters the body cavity but the cutting edges of the obturator blade remain exposed to facilitate cutting.

It is a further benefit of the present invention to provide a trocar in which the piercing tip of the obturator blade is protected by a first shield once it enters the body cavity and the cutting edges of the obturator blade are protected by a second, independently biased, shield once they enter the body cavity.

It is a further benefit of the present invention to provide a trocar that includes a shield that deploys to protect the piercing tip while remaining substantially out of contact with tissue, thus reducing frictional forces between the shield and the tissue, thereby ensuring a controlled entry into the body cavity.

While the present system and method has been disclosed according to the preferred embodiment of the invention, those of ordinary skill in the art will understand that other embodiments have also been enabled. Such other embodiments shall fall within the scope and meaning of the appended claims.

What is claimed is:

1. A surgical obturator comprising:
   a blade with two lateral edges; said lateral edges being angled and sharpened at a distal end of said blade to form an acute angle creating a single vertex, said lateral edges and said vertex being a piercing tip;
   a first shield biased when fully extended to cover said vertex but not all of said piercing tip, said first shield having a diameter less than a diameter of said surgical obturator; and
   a second shield biased when fully extended to cover a portion of said piercing tip but not said vertex; wherein said blade is configured with a semi-circular depression along a longitudinal axis of said blade and said first shield is juxtaposed in said depression of said blade; and wherein said second shield is configured with a semi-circular depression along a longitudinal axis of said second shield and said blade is juxtaposed in said depression of said second shield.

2. The surgical obturator of claim 1, wherein said first shield is biased independently from said second shield.

3. The surgical obturator of claim 1, wherein said blade is configured between said first shield and said second shield.

4. The surgical obturator of claim 1, further including a latching mechanism for latching said first shield and said second shield in their distalmost positions.

5. The surgical obturator of claim 1, further including a latching mechanism for latching said first shield and said second shield in their distalmost positions and an actuating mechanism for releasing said latching mechanism.

6. The surgical obturator of claim 1, further including a first biasing element for biasing said first shield into its distalmost position and a second biasing element for biasing said second shield into its distalmost position.

7. The surgical obturator of claim 6, wherein said first biasing element exerts a stronger force on said first shield than said second biasing element exerts on said second shield.

8. The surgical obturator of claim 1, wherein said lateral edges are serrated.

9. A surgical obturator comprising:
   a blade with two lateral edges; said lateral edges being angled and sharpened at a distal end of said blade to form an acute angle creating a single vertex, said lateral edges and said vertex being a piercing tip;
   a first shield biased when fully extended to cover said vertex but not all of said piercing tip, said first shield having a diameter less than a diameter of said surgical obturator; and
   a second shield biased when fully extended to cover a portion of said piercing tip but not said vertex; wherein said blade is configured with a semi-circular depression along a longitudinal axis of said blade and said first shield is juxtaposed in said depression of said blade; and wherein said second shield is configured with a semi-circular depression along a longitudinal axis of said second shield and said first shield is juxtaposed in said depression of said second shield.

10. The surgical obturator of claim 9, wherein said first shield is biased independently from said second shield.

11. The surgical obturator of claim 9, further including a latching mechanism for latching said first shield and said second shield in their distalmost positions.

12. The surgical obturator of claim 9, further including a latching mechanism for latching said first shield and said second shield in their distalmost positions and an actuating mechanism for releasing said latching mechanism.

13. The surgical obturator of claim 9, further including a first biasing element for biasing said first shield into its distalmost position and a second biasing element for biasing said second shield into its distalmost position.

14. The surgical obturator of claim 13, wherein said first biasing element exerts a stronger force on said first shield than said second biasing element exerts on said second shield.

15. The surgical obturator of claim 9, wherein said lateral edges are serrated.

* * * * *